US011382339B2

(12) United States Patent
Jones

(10) Patent No.: US 11,382,339 B2
(45) Date of Patent: Jul. 12, 2022

(54) PREPARING AND STORING A FREE FLOWING FROZEN SUPPLEMENTARY PRODUCT

(71) Applicant: Stan Jones, Vienna, IL (US)

(72) Inventor: Stan Jones, Vienna, IL (US)

(73) Assignee: Dippin' Dots, LLC, Paducah, KY (US)

( * ) Notice: Subject to any disclaimer, the term of this patent is extended or adjusted under 35 U.S.C. 154(b) by 0 days.

(21) Appl. No.: 15/640,985

(22) Filed: Jul. 3, 2017

(65) Prior Publication Data

US 2018/0064134 A1    Mar. 8, 2018

Related U.S. Application Data

(63) Continuation of application No. 15/258,648, filed on Sep. 7, 2016.

(51) Int. Cl.
| | |
|---|---|
| *A23L 3/375* | (2006.01) |
| *A23G 9/16* | (2006.01) |
| *A23G 9/30* | (2006.01) |
| *B01J 2/04* | (2006.01) |
| *B01J 2/26* | (2006.01) |
| *F25D 25/04* | (2006.01) |
| *F25D 3/11* | (2006.01) |
| *A23G 9/06* | (2006.01) |
| *A23G 9/28* | (2006.01) |
| *A61K 9/16* | (2006.01) |
| *F25B 19/00* | (2006.01) |

(52) U.S. Cl.
    CPC ............. *A23G 9/166* (2013.01); *A23G 9/06* (2013.01); *A23G 9/281* (2013.01); *A23G 9/30* (2013.01); *A23L 3/375* (2013.01); *A61K 9/1682* (2013.01); *B01J 2/04* (2013.01); *B01J 2/26* (2013.01); *F25D 3/11* (2013.01); *F25D 25/04* (2013.01); *F25B 19/005* (2013.01)

(58) Field of Classification Search
    CPC .. B65G 17/061; B65G 17/062; B65G 17/063; A01N 1/0257; A01N 1/0268; A23L 3/375
    See application file for complete search history.

(56) References Cited

U.S. PATENT DOCUMENTS

| | | | |
|---|---|---|---|
| 4,333,318 A | 6/1982 | Tyree | |
| 4,944,162 A | 7/1990 | Lang et al. | |
| 6,539,743 B2* | 4/2003 | Jones | A23G 9/045 62/381 |
| 6,910,587 B2* | 6/2005 | Seyffert | B01D 33/048 209/307 |
| 2011/0039009 A1 | 2/2011 | Jones et al. | |

FOREIGN PATENT DOCUMENTS

GB        2193119 A  *  2/1988  ............... B07B 1/10

* cited by examiner

*Primary Examiner* — John F Pettitt, III
(74) *Attorney, Agent, or Firm* — Stockwell & Smedley, PSC

(57) ABSTRACT

A method of preparing and storing a free-flowing frozen supplementary product, including preparing a supplementary composition for freezing, dripping the supplementary composition into a freezing chamber, freezing the dripped supplementary composition into beads, and transporting the frozen beads by conveyor belt out of the freezing chamber.

12 Claims, 7 Drawing Sheets

PREPARING AND STORING A FREE FLOWING FROZEN SUPPLEMENTARY PRODUCT

This application is a divisional application claiming priority benefit to U.S. patent application Ser. No. 15/258,648, filed on Sep. 7, 2016. The entire contents and disclosures of the above application is incorporated herein by reference.

FIELD OF THE INVENTION

The present invention relates generally to the field of frozen supplementary products and, more particularly, to a unique method of preparing a free-flowing frozen supplementary product, such as confections, ice cream, yogurt, bacteria cultures, such as probiotics, pharmaceuticals, etc.

BACKGROUND OF THE INVENTION

Frozen ice cream and yogurt sales have grown dramatically over recent years. This growth has been achieved primarily through extensive advertising and mass marketing efforts. In particular, dairy cooperatives have been promoting ice cream and yogurt as health foods. In addition, a number of new and developing ice cream parlor franchises have conducted aggressive advertising campaigns in order to firmly establish themselves in the marketplace.

If the rising trend in sales is to continue in today's competitive marketplace, however, it is clear that a more sophisticated product must be developed to attract discriminating consumers. A need is therefore identified for such a product.

SUMMARY OF THE INVENTION

Embodiments of the present invention relate to a method of preparing and storing a free-flowing frozen supplementary product, including preparing a supplementary composition for freezing, dripping the alimentary composition into a freezing chamber, freezing the dripped alimentary composition into beads, and transporting the frozen beads by conveyor belt out of the freezing chamber.

Further embodiments of the present invention include an apparatus for manufacturing cryogenically frozen supplementary beads, including a freezing chamber containing a cryogenic liquid, at least one feed tray overlying the freezing chamber arranged and adapted to receive liquid composition from a delivery source, the tray having a plurality of orifices for the discharge of uniformly sized droplets of the composition from the feed tray, whereby the droplets are delivered by gravity into the freezing chamber there-below to form frozen beads, a conveyor belt assembly comprising a conveyor belt positing at the bottom of the freezing chamber.

Additional embodiments of the present invention include a transport assembly for a cryogenic processor, including an elongated housing forming a channel for the delivery of a frozen product from an intake end to a chute at a discharge end, the elongated hosing configured to receive the frozen product from the cryogenic processor, a conveyor belt disposed within the elongated housing for movement of the frozen product from the intake end to the discharge end, a drive motor assembly configured to rotate the conveyor belt, and an openable cleaning drain line disposed near the intake end of the elongated housing.

DETAILED DESCRIPTION OF THE PREFERRED EMBODIMENTS

Figure 1:
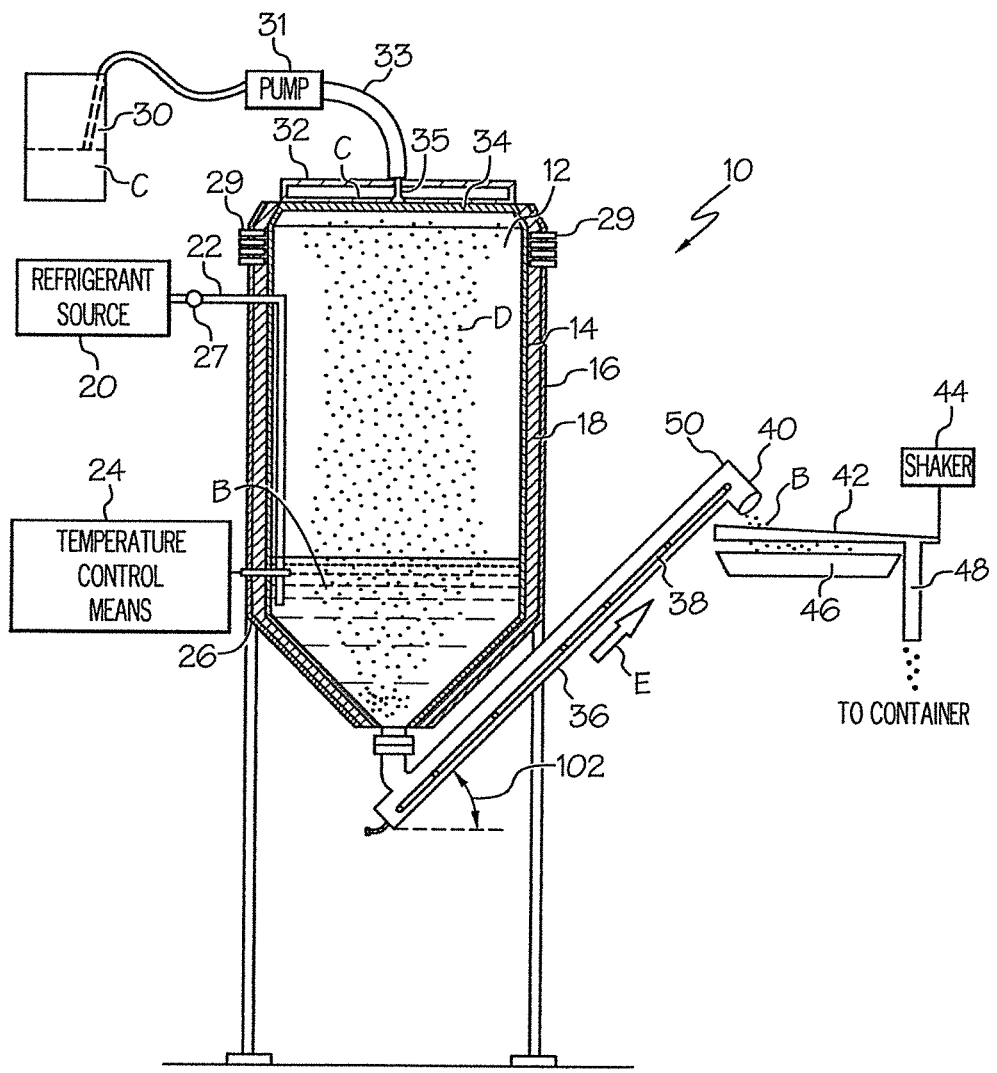
FIG. 1 depicts a diagram cross-sectional view of an apparatus for preparing the free-flowing, frozen supplementary product in accordance with the principles of the present invention.

Previous methods and apparatuses for manufacturing cryogenically frozen beads contain an auger to transport the beads from a cryogenic liquid refrigerant in a bottom of a chamber to a shaker and from the shaker to a container for packaging. However, transportation of the beads by an auger grinds some of the beads against the outer wall of the surrounding tube. The ground beads may become smaller than desired for the end product, and therefore must be separated using a shaker before packaging. Thus, transporting the beads without grinding the beads may be desirable, such that separating the beads using a shaker may no longer be necessary.

"About," as used in this application, means within plus or minus one at the last reported digit. For example, about 1.00 means 1.00±0.01 unit.

"Around," when used to describe a unit or percentage, means within plus or minus one unit or plus or minus one percentage point.

"Proximate," when used to describe position of an element relative to one object of a set of multiple objects, conveys that the element is positioned closer to the one object than any other object of the set.

"Substantially," as used in this application with reference to an angle, means within one degree. For example, substantially planar means within one degree counterclockwise and within one degree clockwise of planar orientation.

"Substantially," as used in this application with reference to a shape, means within manufacturing tolerance of manufacturing the referenced shape as well as any other shape falling within the doctrine of equivalents for the referenced shape.

"Substantially similar," as used in this application, means having at least each of the properties of the referenced structure plus the additional structure disclosed. If the additional structure conflicts, the additional structure supersedes the structure incorporated by reference.

"Free-flowing," as used herein, is a broad term which includes the ability of the product to flow as individual beads, with little or no clumping or sticking to each other, during such pouring. There may be slight sticking after a period of storage, but a light tap on the container may unstick the beads and allow them to be free-flowing. The generally spherical shape helps contribute to the free-flowing, pourable product. It may be desired that the beaded product is in a free-flowing format so that it is readily pourable.

"Supplementary," as used in this application, means at least one of alimentary, comestible, pharmaceutical, and probiotic.

"Sanitary roller," as used in this application, means either a shielded roller or an open roller. Shielded sanitary rollers may comprise a mechanism to prevent and/or restrict the entry of fluid into the roller. For example, shielded sanitary rollers may comprise one or more reciprocating, rotary, or oscillating seals. Example seals include an O-ring, a double O-ring, an X-ring, a square-ring, and/or a U-cup. Furthermore, each seal may be situated in a corresponding groove such that the seal maintains contact with the roller and/or housing. Open sanitary rollers may comprise openings that allow fluid to pass through the roller. Open rollers may allow for easy cleaning by passing fluid through the roller.

For the purposes of this disclosure, "and" and "or" shall be construed as conjunctively or disjunctively, whichever provides the broadest disclosure in each instance of use of "and" and "or."

For the purposes of this disclosure, structures disclosed in singular form are not limited to a single structure, but can include multiple instances of the disclosed structure, unless specifically stated otherwise.

The detailed description set forth below in connection with the appended drawings is intended as a description of various embodiments of the invention and is not intended to represent the only embodiments in which the invention may be practiced. The detailed description includes specific details for the purpose of providing a thorough understanding of the invention. However, it will be apparent to those skilled in the art that the invention may be practiced without these specific details. In some instances, well known structures and components are shown in block diagram form in order to avoid obscuring the concepts of the invention.

FIG. 1 depicts a diagram of a cross-sectional view of an apparatus 10 for preparing the free-flowing, frozen supplementary product in accordance with the principles of the present invention. It should be recognized that this apparatus 10 is merely being described as an example of one type of apparatus designed for this purpose. Other designs may, of course, be utilized in accordance with the present method to produce the free-flowing, frozen supplementary product.

As shown, the apparatus 10 can include a freezing chamber 12 having an inner wall 14 and outer wall 16. In some embodiments, both the walls 14 and 16 may be constructed of stainless steel to provide both strength and corrosion resistance. However, the walls 14 and 16 may comprise any material sufficient to withstand cryogenic temperatures while retaining the structural integrity of the freezing chamber 12. A thick layer of thermal insulating construction 18 may be provided between the walls 14, 16 to improve the efficiency of the freezing chamber by reducing the thermal transfer through the walls 14, 16 between the interior of the chamber 12 and the ambient environment. In some embodiments, the thermal insulating construction 18 may include an insulating material, such as fiberglass. Other embodiments include a thermal insulating construction 18 comprising a vacuum between the walls 14, 16.

The chamber 12 may be chilled by the direct addition of refrigerant from a refrigerant source 20 through the delivery line 22. A number of different refrigerants can be utilized, including liquid nitrogen. Liquid nitrogen is readily available, relatively inexpensive and relatively inert to food products. It is also sufficiently cold to provide for relatively rapid freezing of the product. As such, it is particularly adapted for utilization in the processing of free-flowing, supplementary products in accordance with the present invention.

The temperature of the freezing chamber as well as the level of liquid refrigerant may be maintained within a specified range through the utilization of a temperature control means 24 such as a thermostat as is known in the art. More specifically, the temperature control means 24 may be connected to a thermocouple 26. The thermocouple 26 may be positioned to extend into the freezing chamber 12 at a selected height between, for example, 4 to 18 inches above the bottom of the chamber to sense the temperature within the chamber. Where, for example, liquid nitrogen is utilized as the refrigerant, the thermostat may be set to maintain the temperature within the chamber 12 at a thermocouple 26 between approximately −184° C. (−300° F.) to approximately −195° C. (−320° F.). The positioning of the thermocouple 26 some 4 to 18 inches above the bottom of the chamber 12 may provide the necessary reservoir of refrigerant to quick freeze the droplets of the supplementary composition. The ultra-low temperature of the refrigerant can limit the formation of ice crystals in the product as it is frozen. Advantageously, by reducing the overall size of the ice crystals being formed, the resulting frozen product may have a richer, creamier texture and exhibit a better overall flavor.

For example, when the temperature within the chamber 12 at the thermocouple 26 rises above the set range of operation (i.e. −300° to −320° F.), this can be an indication that the level of liquid refrigerant has fallen below the thermocouple. As a result of the operation of the temperature control means 24, a valve 27 may then be opened to allow delivery of liquid nitrogen from the source 20 through the line 22 to the chamber 12. Once the liquid refrigerant level within the chamber 12 reaches and contacts the thermocouple 26, the desired level of liquid refrigerant for freezing the composition is restored and the valve 27 may be closed.

Of course, alternative temperature or level control systems may be utilized. For example, a number of thermocouples 26 may be positioned at various heights within the chamber 12. The thermocouple 26 at the desired liquid refrigerant level to be maintained can then be selected and utilized as described above. In another alternative, a liquid nitrogen level controller such as manufactured and marketed by Minnesota Valley Engineering, Inc. under the trademark CRYO-MED (Model LL-450) may be utilized.

Vents 29 may be provided in the walls 14, 16 near the top of the freezing chamber 12. These vents 29 may serve to release rising nitrogen vapor from the chamber 12 and may prevent any build-up in pressure in the chamber or any excess lowering of temperature near the top such that the dropper system is frozen over time. This exhaust can be controlled manually by venting through an exit pipe which may be controlled by a damper. Alternatively, the exhaust gas can be collected under vacuum by the use of an exhaust fan. This cold vapor can be routed to other parts of the process where cold vapors can be utilized such as in storage spaces or with packaging machines.

The first step of a method of the present invention may be to prepare a supplementary composition for freezing. In some embodiments, the composition may be dairy based and can include such ingredients as cream, milk, butter and/or eggs. Additional ingredients could include sugar, fruit extracts or some other flavoring component, such as vanilla extract. However, embodiments include probiotic formulations, pharmaceutical formulations, non-dairy based formulations for forming frozen confectionary beads, etc.

After preparing the composition comes the step of slowly dripping the composition into the freezing chamber 12. This may be accomplished in a number of ways. For example, as shown in FIG. 1, the composition C may be pumped from a supply container 30 into a dropper system including a tray 32 positioned across the upper end of the freezing chamber 12. More specifically, the composition may be pumped by pump 31 through the tube 33 so as to be delivered through an inlet 35 in the top of the tray that closes the tray to prevent any residual dirt or dust in the air from falling into the composition. The bottom of the tray 32 can include a series of apertures 34 through which the composition drips into the freezing chamber 12. The apertures may have a diameter of between about 0.3175 cm (0.125 inches) and 0.794 cm (0.3125 inches) so as to provide the desired size droplets of composition for freezing into beads. Of course, the size of the droplets and rate of flow may be determined not only by the size of the holes, but the thickness of the composition and in some cases the thickness of the tray.

As the droplets D of composition fall downwardly in the freezing chamber, they contact cold nitrogen gas rapidly vaporizing from the pool of liquid nitrogen P at the bottom of the chamber 12. As a result of the temperature within the range of $-162°$ C. ($-260°$ F.) to $-195°$ C. ($-320°$ F.) (for liquid $N_2$), rapid freezing of the droplets of composition occurs. The small beads B that are produced might contain only relatively small ice crystals. The beads B may have a smooth, spherical appearance.

A conveyor belt assembly 50 for collecting the beads B may extend into the bottom of the chamber 12 at an intake end of an elongated housing 36. The conveyor belt assembly 50 may comprise a conveyor belt 38 within the housing 36. Furthermore, the conveyor belt 38 may extend from the intake end of the housing 36 to a discharge end comprising a chute 40. As shown, the conveyor belt 38 may be positioned at a conveying angle 102 ranging from approximately 55° to approximately 60° with respect to the horizontal plane. As depicted, the conveyor belt 38 may be substantially parallel to the housing 36. The horizontal plane refers to the plane that is perpendicular to the lengthwise plane of the apparatus 10. Furthermore, the horizontal plane may be parallel to the ground when the apparatus 10 is in upright position upon the ground. Embodiments of the present invention also include an angle of approximately 50° from the horizontal plan, and 45° from the horizontal plane. The conveyor belt 38 can include transport structures (not illustrated in FIG. 1) that move the beads B against gravity out of the bottom of chamber 12 through the chute 40.

As the conveyor belt 38 is rotated, the beads B may be drawn upwardly in the direction of action arrow E on the conveyor belt 38 and/or transport structures. Liquid refrigerant, however, may not necessarily be withdrawn from the freezing chamber 12 as the liquid nitrogen may drain back to the pool P.

Conveyor belt 38 may be comprised of any material that is resilient while bending under cryogenic conditions. Example materials include rubber and linked metal constructions. In embodiments having linked metal constructions. Small holes between the metal links may be used to strain the cryogenic liquid from the beads B back to chamber 12.

Once the beads B reach the top of the conveyor belt 38, they may be deposited by means of a chute 40 onto a sieve 42. The sieve 42 may be connected to a shaking apparatus 44 as is known in the art. This shaking apparatus 44 can vibrate the beads B on the sieve 42. Thus, sifting of the beads B may occur with the relatively large beads having a diameter of, for example, approximately 2 mm or larger remaining on the surface of the sieve while the smaller beads and fragmented portions of broken beads may fall through the sieve into the collecting pan 46. That material collected in the pan 46 may be melted and reprocessed by mixing back in with the composition C that is added to the tray 32 as described above.

The appropriately-sized beads (e.g. diameter of greater than 2 mm) may flow over the sieve to a discharge chute 48 where they may be deposited into a container (not shown). This container may be maintained open for substantially 1-10 minutes in order to allow any residual nitrogen refrigerant retained in or on the surface of the beads to vaporize. Then, the container may be sealed and placed in a freezer for storage.

In order to prevent the beads B from sticking together during storage and thereby maintain their free-flowing character, they can be maintained at a relatively low temperature. More specifically, if the beads B are to be stored for greater than a period of approximately 30 hours, they should be stored in the refrigerator at a temperature of at least as low as $-28.9°$ C. ($-20°$ F.). More preferably, the beads are stored at a temperature between $-1.1°$ C. ($-30°$ F.) and $-40°$ C. ($-40°$ F.).

Alternatively, if the beads B are to be consumed within a 30-hour period (or shorter period of 10-12 hours for certain compositions), they can be stored in the freezer at a temperature of $-28.9°$ C. ($-20°$ F.) or above. However, the beads B can be brought to a temperature between about $-23.3°$ C. ($-10°$ F.) and $-28.9°$ C. ($-20°$ F.), with $-26.1°$ C. ($-15°$ F.) providing good results. Warmer temperatures may result in the beads sticking together and the product losing its unique free-flowing property, thus reducing its consumer appeal. When served at a colder temperature, many individuals may find that the product is too cold to be fully enjoyed.

Figure 2:
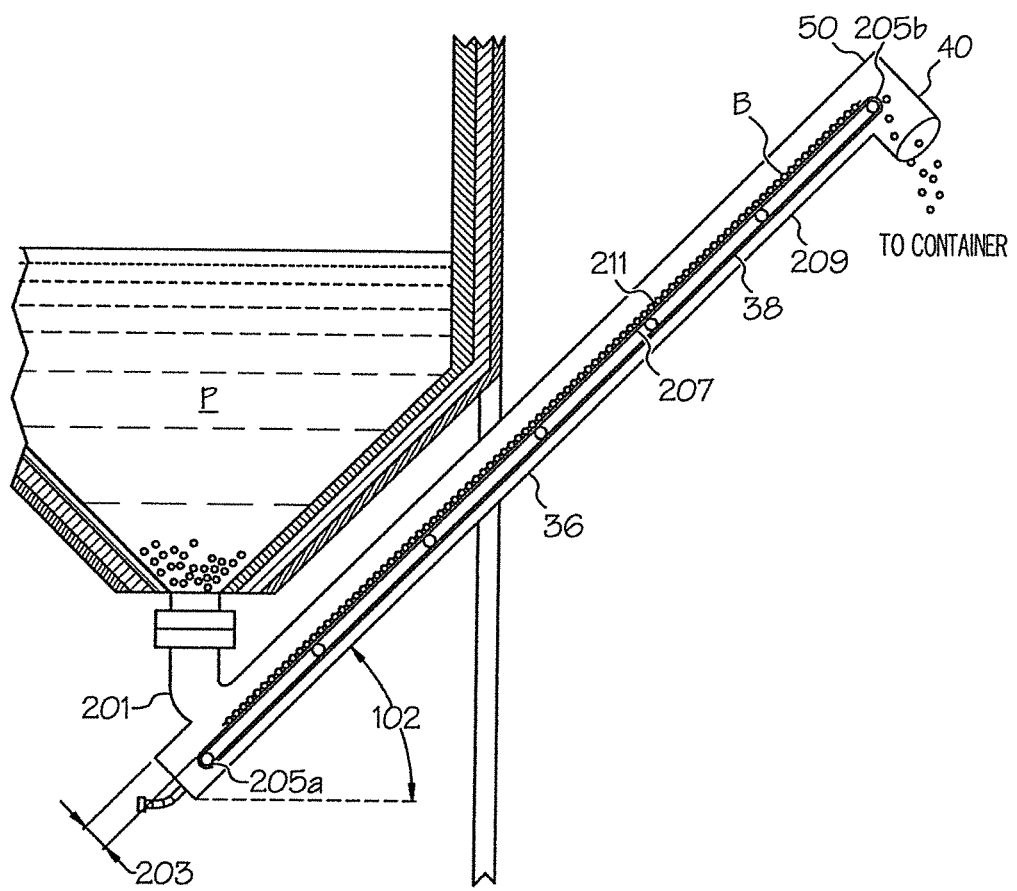
FIG. 2 depicts a diagram of a cross-sectional view of the apparatus of FIG. 1 with greater detail of a conveyor belt of the apparatus in accordance with the principles of the present invention.

FIG. 2 depicts a diagram of a cross-sectional view of the apparatus of FIG. 1 with greater detail of a conveyor belt 38 of the apparatus 10 in accordance with the principles of the present invention. For example, conveyor belt 38 may comprise a belt 207 frictionally fit around one or more rollers, 205a and 205b. The rotation of either roller 205a or 205b may drive the rotation of the belt 207. By way of example, 205b may be a drive roller and 205a may be a support roller. Furthermore, the rotation of the belt 38 may drive beads B from the bottom of chamber 12 to the chute 40. In some embodiments, a retaining wall 201 may be spaced a straining distance 203 from the outside of the belt 207. The straining distance 203 may be sized at less than 2 mm, such that frozen beads 2 mm in diameter or larger are corralled onto the belt 207. In some embodiments, the smaller beads are not carried by the belt 207 to chute 40.

Furthermore, some embodiments of the conveyor belt 38 do not grind the beads B into smaller beads, such as by preventing grinding the beads B between an auger flight and the outer tubing 209 of housing 36. Thus, some embodiments implementing the conveyor belt do not necessarily require a sieve 42 and shaker 44 for separating beads having greater than or equal to 2 mm diameter from those with a smaller diameter.

As can be seen, guide rails 211 may be provided along both sides of the conveyor belt to guide the transport of the frozen beads B to the chute 40. Guide rails 211 may comprise any material of sufficient rigidity to guide the frozen beads B with a tolerance of cryogenic temperatures. Examples include composites, certain rubbers, certain polymers, metals, etc.

In addition, the conveyor belt 38, 207 may be configured at a conveying angle 102. The conveying angle 102 may aid in transportation of appropriately sized beads, draining cryogenic liquid, and/or removal of inappropriately sized beads. For example, the conveying angle 102 may be approximately 55° to approximately 60° degrees from horizontal.

Figure 3:
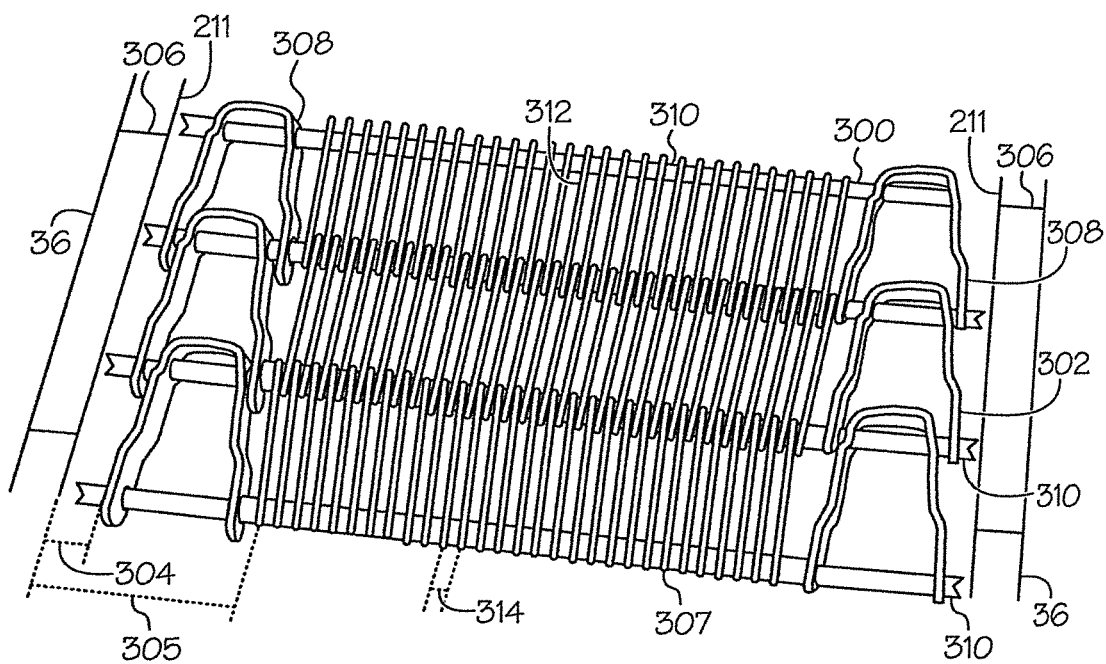
FIG. 3 depicts a top-down view diagram of a mesh conveyor belt for use with the apparatus of FIG. 2 in accordance with the principles of the present invention.

FIG. 3 depicts a top-down view diagram of a mesh conveyor belt 300 for use with the apparatus of FIG. 2 in accordance with the principles of the present invention. The mesh conveyor belt 300 may comprise metal, such as steel, plastics, composites, rubber, cloth, etc. As can be seen in FIG. 3, the conveyor belt 300 may comprise links 302. The links 302 may comprise crossbars 310 connected by wing hinges 308. In fact, crossbars 310 may extend through respective holes of wing hinges 308. Crossbars 310 may be pivotally connected with the respective wing hinges 308.

Furthermore, rods 312 may extend between two respective crossbars 310. Rods 312 may be in pivotal relationship with both respective crossbars 310. The rods 312 may also be spaced apart by a rod gap 314. The rod gap 314 may be sized to retain beads B on the conveyor belt 300 during transport. Furthermore, the rod gap 314 may allow fluids to pass through. In some embodiments, rod gap 314 may allow inappropriately small beads to pass through. Therefore, rod gap 314 may be less than 2 mm between respective rods 312, such that appropriately-sized beads are transported from chamber 12 to chute 40.

The diameter of each crossbar 310 may extend orthogonally from the outer surface of the conveyor belt 300. For example, rod gaps 314 may be a transport structure for pushing the beads as the surface of conveyor belt 300 moves from chamber 12 to chute 40. The number, size, and surface area population density of the rod gaps 314 on the conveyor belt 300 may be selected to control the size and rate of transport of beads B. Furthermore, the rotation speed of the conveyor belt 300 may be altered to manipulate the uptake of beads B.

The mesh 307 of the conveyor belt 300 may comprise the area of the intersections of the rods 312 and the crossbars 310.

The guide rails 211 may be substantially parallel with the belt 300 and may be positioned relative to the belt 300. For example, the guide rails 211 may be positioned to retain the frozen beads B on the conveyor belt 300. Thus, the guide rails 211 may be positioned slightly above the conveyor belt 300. Furthermore the guide rails 211 may be set apart slightly wider than the width of the conveyor belt 300. Therefore, a guide span 304 may describe the distance from an outer edge of the conveyor belt 300 to the nearest surface of the nearest guide rail 211. Because the guide rails 211 may be configured to retain beads B on the conveyor belt 300 as the beads B travel to the chute 40, the guide span 304 may be sized such that beads B of a predetermined size may be retained on the conveyor belt 300. Thus, the guide span 304 may be 2 mm or less, in order to allow very small beads to fall off. In some embodiments, the guide span 304 may be 4 mm or less. Guide span 304 may also be negative when the wing hinges 308 are sized such that appropriately-sized beads B may fall through the wing hinges 308.

In some embodiments, the guide rails may be positioned above the mesh 307. Therefore, mesh guide span 305, describing the distance from the outside of the mesh 207 to the outside of the respective guide rail 211 may be less than 2 mm, or even negative when the guide rails 211 are positioned within the outer bounds of the mesh 307.

The guide rails 211 may be attached to supports 306 that may be attached to the inside surface of the surrounding housing 36. In additional embodiments, the attachment of the guide rails 211 to the supports 306 may be removable such as by pins, clips, or other attachment mechanism. This attachment mechanism of the supports 306 can include a permanent anchor rail that runs down the interior of the housing 36. The anchor rail may be parallel beside the side of the conveyor belt 300 and may run the length of the conveyor belt 300. The anchor rail may contain a lengthwise female grove in which a male groove of the removable guide rail 211 may be inserted to position the guide rail 211 for operation of guiding the beads B along the conveyor belt 300. Alternative embodiments include a female anchor rail running a portion of the length of the housing and attached to the supports 306 for receiving the guide rail 211.

Rod gaps 314 may comprise recesses in the conveyor belt 300. In some embodiments, rod gaps 214 may comprise holes through the conveyor belt 300 such that the beads B are strained from the cryogenic liquid. Furthermore, cleaning fluids may pass through rod gaps 214.

Figure 4A:
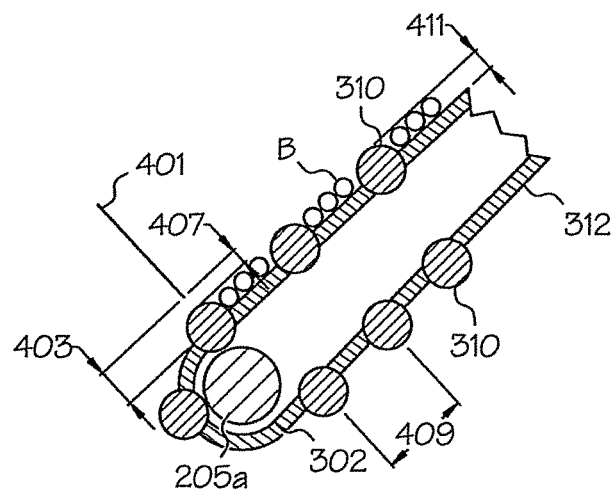
FIG. 4A depicts a cutaway side-view diagram of the conveyor belt of FIG. 3 in accordance with the principles of the present invention.

FIG. 4A depicts a cutaway side-view diagram of the conveyor belt 300 of FIG. 3 in accordance with the principles of the present invention. Retaining wall 401 may be similar in all respects to retaining wall 201. Furthermore, retaining wall 401 may be spaced similarly to retaining wall 201. Thus, straining distance 403 may be similar to straining distance 203. In addition, gap 407 may be a distance between the top of respective crossbars 310, as they pass under retaining wall. Gap 407 may be sized to allow fluid to pass through. Furthermore, gap 407 may allow very small beads to pass through.

Selection of the beads B may occur by the size and shape of the rod gaps 314. For example, beads B having a diameter of about 10.0 mm or larger may be selected by rod gaps 314 sized 10.0 mm or larger. Additionally, beads B having a diameter of about 4.0 mm or larger may be selected by rod gaps 314 of 4.0 mm or less. Furthermore, beads B having a diameter of about 2.0 mm or larger may be selected by rod gaps 314 of 2.0 mm. Smaller diameter beads B may pass through rod gaps 314 larger than the diameter of the smaller diameter beads.

Link span 409 may represent the distance between respective crossbars 310. Link span 409 may be sized to regulate the uptake density of beads B. For example, an oversized link span 409 may not maximize uptake density due to beads B crowding and falling over the lower crossbar 310. However, an undersized link span 409 may reduce the transporting surface area of the mesh 307 by including unnecessary crossbars 310 (if crossbars 310 are configured such that beads B don't rest directly on the crossbars 301, thereby reducing available surface area of the conveyor belt 300 for transport). Link span 409 may be predetermined according to the diameter of crossbars 310.

Crossbars 310 may extend orthogonally from the surface of belt 300 at a crossbar height 411. The crossbar height may be predetermined to allow for pushing the beads B as the conveyor belt 300 moves. For example, crossbar height 411 may be larger than the diameter of the corresponding beads B. However, crossbar height 411 may be as small as one eighth of the diameter of corresponding beads B, depending on the conveyor belt angle 102. Using a smaller crossbar height 411 may increase transport surface area of the conveyor belt 300.

Based on the configuration of the conveyor belt mesh 307, the rod gaps 314, the straining distance 403, the gap 407, the retaining wall 401, and/or the crossbar height 411, beads B of a predetermined size may be sifted from the frozen beads B. For example, beads of a 2.0 mm diameter may be sifted. In some embodiments, beads having a diameter of about 2.0 mm to 10.0 mm may be sifted from the remaining beads.

Figure 4B:
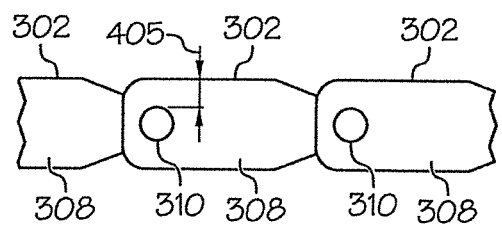
FIG. 4B depicts a side-view diagram of the conveyor belt of FIG. 3 in accordance with the principles of the present invention.

FIG. 4B depicts a side-view diagram of the conveyor belt 300 of FIG. 3 in accordance with the principles of the present invention. Specifically, the interaction of three links 302 is depicted. Respective crossbars 310 extend through each respective wing hinge 308. Furthermore, wing hinges 308 may extend orthogonally from the surface of the conveyor belt 300 at a guide height 405. This guide height 405 may be sufficient to retain appropriately-sized beads B on the conveyor belt mesh 307. For example, guide height 405 may be at least one-eighth of the diameter of the corresponding beads B. Guide height 408 may be larger than the diameter of the corresponding beads B.

Figure 5:
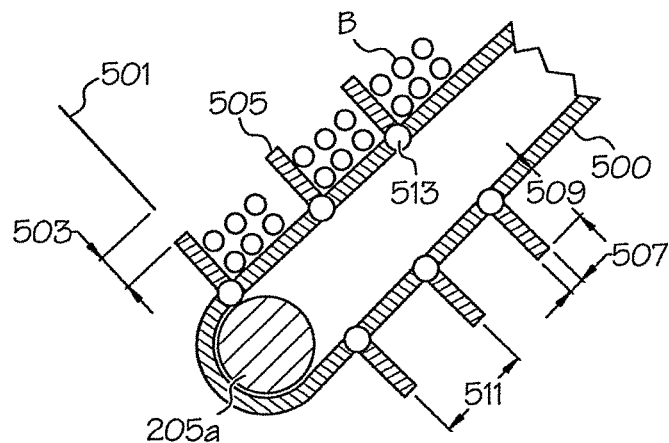
FIG. 5 depicts a diagram of a side view of an alternative conveyor belt for use with the apparatus of FIG. 2 in accordance with the principles of the present invention.

FIG. 5 depicts a diagram of a side view of an alternative conveyor belt 500 for use with the apparatus 10 of FIG. 2 in accordance with the principles of the present invention. Conveyor belt 500 may comprise transport structures, such as cleats 505. Cleats 505 may aid the rods 312 and crossbars 310 in transporting the beads B on the conveyor belt 500. Therefore, cleats 500 may be any transport structure for transporting beads B from chamber 12 to chute 40. For example, cleats 505 may span the width of the conveyor belt 500. Cleats 505 may extend orthogonally from crossbars 301 or from rods 312. Cleats 505 may span a width of the conveyor belt 500 and may extend orthogonally from an outer surface of the conveyor belt 500. Furthermore, the cleats 505 may be set apart along the conveyor belt 500 at a predetermined spacing 511. The cleats 505 may have a height 509, and a thickness 507. The height 509 and spacing 511, in conjunction with the belt speed, may be correlated with the rate of formation of the beads B or the desired transportation rate of the beads B. In some embodiments, selection of the beads B may occur by the size of the cleats 505 in conjunction with the size of spacing 511.

Furthermore, retaining wall 501 may be placed such that the beads B are guided by the operation of gravity onto the conveyor belt 500 and between the cleats 505. Retaining wall 501 may be positioned within a retention distance 503 of the tops of the respective cleats 505 when the cleats 505 pass under retaining wall 501. The retention distance may be less than the diameter of the smallest beads that are desired (e.g. less than 2 mm diameter).

In some embodiments, the cleats 505 may be constructed of solid materials that are resilient under cryogenic conditions, such as rubber, metals, and/or composites. However, other embodiments of the cleats 505 include mesh constructions, such that the cleats 505 strain the beads B from the cryogenic liquid. The cleats 505 may extend orthogonally from the conveyor belt 500 and between the guide rails 211 such that the beads B on the conveyor belt 500 are confined to the space between two cleats 500 and the two guide rails 211.

Based on the configuration of the conveyor belt mesh of conveyor belt 500, the corresponding rod gaps, the retention distance 503, the retaining wall 501, and/or the configuration of the cleats 505, such as cleat height 509, beads B of a predetermined size may be sifted from the frozen beads B. For example, beads of a 2.0 mm diameter may be sifted. In some embodiments, beads having a diameter of about 2.0 mm to 10.0 mm may be sifted from the remaining beads.

Figure 6:
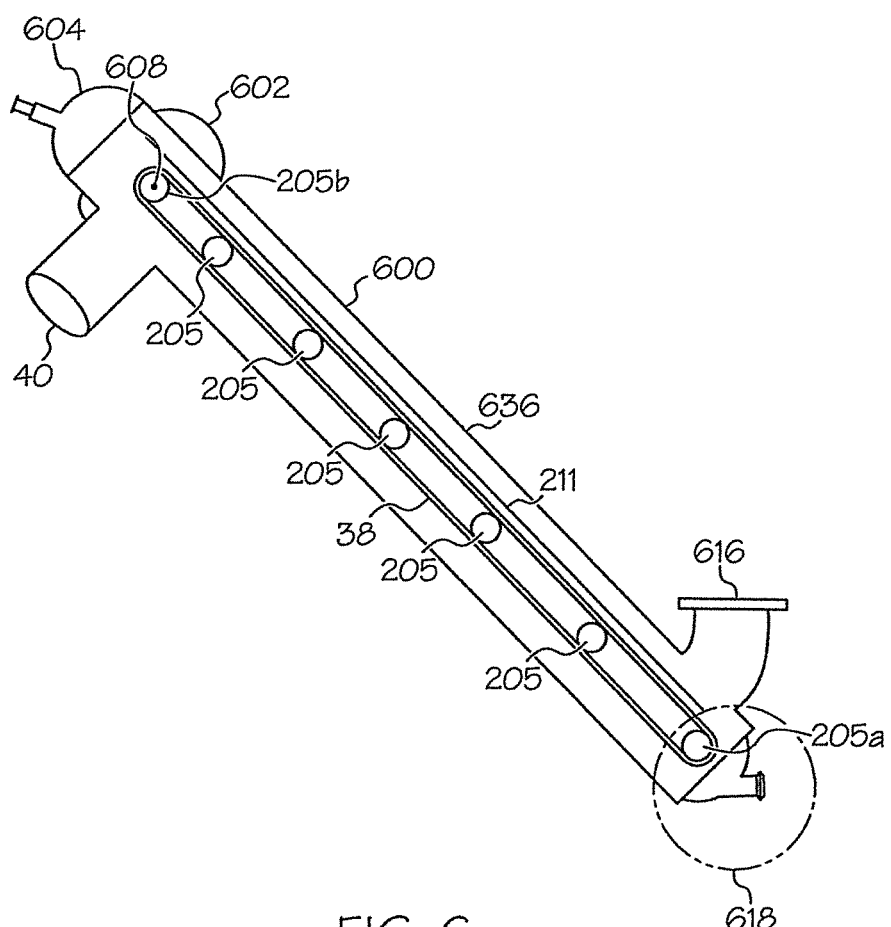
FIG. 6 depicts a side view of a conveyor belt assembly in accordance with the principles of the present invention.

FIG. 6 depicts a side view of a conveyor belt assembly 600 in accordance with the principles of the present invention. In some embodiments, the conveyor belt assembly 600 may be substantially similar to the conveyor belt assembly 50.

Conveyor belt assembly 600 may comprise a motor 602 that is in rotatable communication with roller 205b, such as via a rotary assembly 612. Thus, roller 205b may be rotatably driven by motor 602. For example, motor 602 may cause rotation of belt 604 about roller 205b. Roller 205b may share common axle 608 with motor 602. Thus, rotation of belt 38 may drive rotation of support rollers 205, such as roller 205a. Roller 205b and support rollers 205, 205a may be rotatably connected via frictional fit with belt 38. Support rollers 205 may be substantially similar to support roller 205a.

Furthermore, conveyor belt assembly 600 may comprise intake 616. Intake 616 may receive the beads B such that belt 38 may transport the beads to chute 40. The intake 616 may receive material, such as frozen beads B, which may be fed from the chamber 12 to intake 616 by the operation of gravity.

Conveyor belt assembly 600 may further comprise bell hub 604. Bell hub 604 may comprise a connector for receiving cleaning fluids, such as water, detergent, and/or disinfectant. Thus, conveyor belt assembly 600 may be a clean-in-place assembly. A "clean-in-place assembly" and a "clean-in-place configuration" mean that the conveyor belt assembly 600 can be cleaned by pumping cleaning fluids, such as water, soap, detergents, disinfectants, etc., through the clean-in-place conveyor belt assembly 600 without removing the conveyor belt assembly 600 from the apparatus 10. Furthermore, cleaning fluids may clean each of the structures within the housing 636. As the assembly 600 is cleaned, fluids may flow to the intake end 618. The fluids may be released from the intake end 618 via a drain line (explained with respect to FIG. 7).

Figure 7:
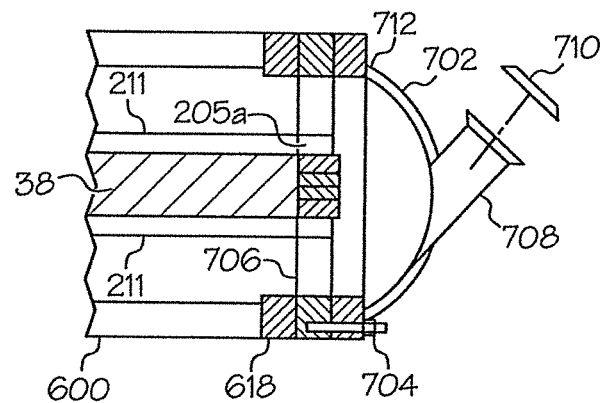
FIG. 7 depicts a view of the intake end of the conveyor belt assembly in accordance with the principles of the present invention.

FIG. 7 depicts a view of the intake end 618 of the conveyor belt assembly 600 in accordance with the principles of the present invention. By way of illustration, an axle 706 is depicted at a vertical angle relative to a drain 708 rather than the alternative horizontal angle depicted in FIG. 6. Thus, axle 706 may rotatably engage roller 205a such that belt 38 is turned when axle 706 is turned.

Intake end 618 may be joined to cover 712. For example, intake end 618 and cover 712 may be frictionally fit, joined with a bolt 704, etc. For example, cover 712 may comprise dome 702, such that incorrectly sized particles and/or other debris may be contained. Thus, drain line 708 may be used to remove the incorrectly sized particles, debris, cleaning fluids, and/or other waste. For example, cap 710 may be place over drain line 708 such that any contained liquid nitrogen, beads, etc. does not drain during operation. However, operation may be temporarily ceased for cleaning. Drain line 708 may be connected to a hose for rinsing intake end 618 with water, soap, rinse solutions, and/or disinfectants. Alternatively, water, soap, rinse solutions, and/or disinfectants may be passed into the conveyor belt assembly 600 through the chute 40 and/or bell hub 604.

While the conveyor belt assembly 600 is in operation conveying material, the drain line 708 may remain closed, for example by securely but removably attaching the drain cap 710 to the drain line 708. In one embodiment, the drain cap 710 may be removably attached to the drain line 708 with sanitary Tri-Clamp fittings. For example, Tri-Clamp ferrule P/N L14AM7 may be used for the drain line 708. In this embodiment, the drain cap 710 is Tri-Clamp solid end cap P/N 16AMP. A Tri-Clamp gasket P/N 40MP-UW is inserted between the drain line 708 and the drain cap 710, and Tri-Clamp single pin heavy duty clamp P/N 13MHHM removably secures the drain cap 710 to the drain 708.

Figure 8:
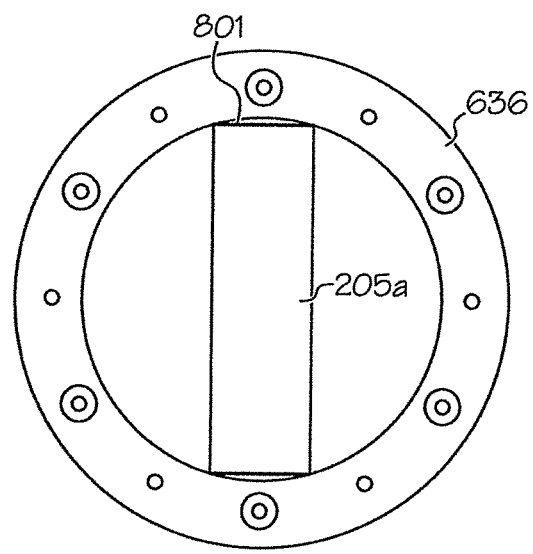
FIG. 8 illustrates another view of the intake end of the conveyor belt assembly in accordance with the principles of the present invention.

FIG. 8 illustrates another view of the intake end 618 of the conveyor belt assembly 600. This embodiment includes a sanitary roller 205a that comprises a solid material. In some embodiments, all the rollers 205, 205a, and 205b comprise sanitary rollers. Sanitary roller 205a may extend from one side of the housing 636 to the opposite side. The axle is not depicted and is further explained with respect to FIG. 10. Sanitary roller 205a may be protected by one or more O-rings 801 at the intersection of the housing 636 and the roller 205a. Furthermore, support rollers 205 may comprise sanitary support rollers 205a.

Debris could fall from material conveyed by the conveyor belt assembly 600, accumulating around the axle 706 and roller 205a. Therefore, some embodiments include solid construction of the roller 205a and the axle 706 comprising composite materials, such as Teflon. Furthermore, gaskets 801 may be situated on the axles 706 and on both sides of the rollers 205, 205a, 205b. The gaskets 801 may seal the bearings, or other rotation mechanism, of the rollers 205, 205a, 205b such that debris is prevented from entering the bearings. Example gaskets include O-rings or other gaskets and may comprise composites, Teflon, rubber, silicone, metal, etc. For example, Teflon axles 706 with an O-ring gasket positioned on the outside of the rollers, such as rollers 205a, 205b, the unmarked support rollers, and any undepicted rollers, may keep the rollers clean, operable, and easy-to-clean.

In some embodiments, the conveyor belt assembly 600 may be readily cleaned without dismantling. To clean the conveyor belt assembly, the drain line 710 may be opened, and wash and rinse solutions and disinfectants may be passed into the housing 636 through the chute 40 and/or the intake 616. Alternatively, a nozzle may be provided at the outlet end of the conveyor belt assembly 600 for accepting wash and rinse solutions. The wash and rinse solutions and disinfectants may flow downward against the belt 38 and rollers 205, 205a, 205b, passing freely between the axle 706 of the roller 205b, and exiting from the drain line 708. The currents or fluid flow forces created by the cleaners and disinfectants may effectively remove debris from the intake end 618, allowing the conveyor belt assembly 600 to be cleaned without dismantling. When removal of the cover 712 is required to allow inspection of the interior of the intake end 618, the axle 706 can be advantageously attached to the housing 636, allowing removal of the cover 712 without destabilizing the conveyor belt 38.

Figure 9:
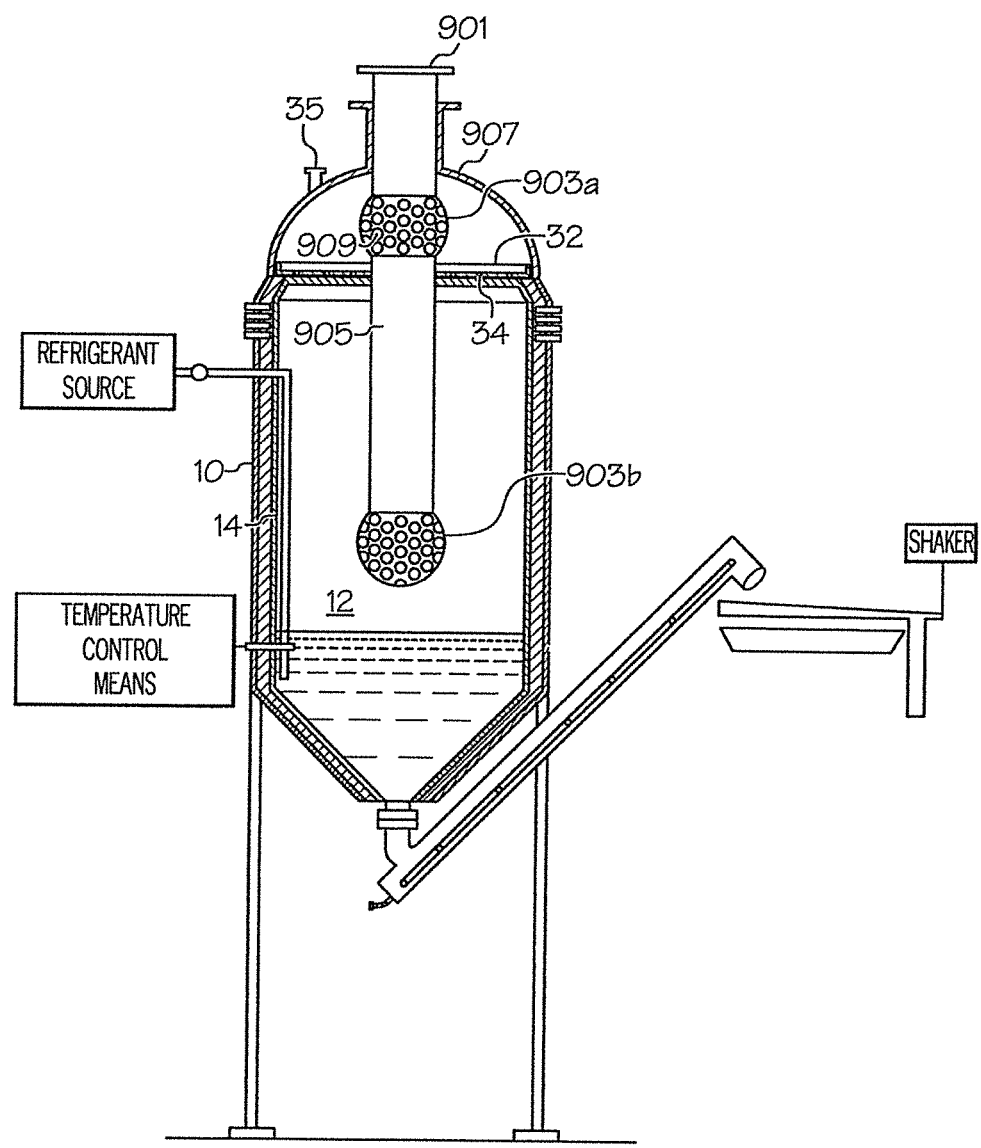
FIG. 9 depicts the apparatus of FIG. 1 comprising a self-cleaning extension.

FIG. 9 depicts the apparatus 10 of FIG. 1 comprising a cleaning extension 905. As can be seen, the cleaning extension 905 may extend into chamber 12 of apparatus 10. Thus, apparatus 10 may comprise a clean-in-place configuration, wherein cleaning fluids can be pumped through apparatus 10 without disassembly of apparatus 10. Cleaning extension 905 may comprise one or more spray balls 903a and 903b. Additionally, each spray ball 903a and 903b may comprise respective sets of holes 909. Each respective hole 909 may be in fluid communication with intake 901 through the cleaning extension 905. In this manner, cleaning solution comprising may be pumped into the cleaning extension 905, through the respective holes 909 of the spray balls 903a and 903b in order to clean the interior of apparatus 10. In some embodiments, the cleaning solution may comprise water. In addition, the cleaning solutions may comprise one or more detergents.

In some embodiments, a first spray ball 903a may be positioned over the drip tray 32 such that water and/or detergents may be sprayed onto drip tray 32 and through apertures 34 during cleaning. Top 907 may enclose spray ball 903a such that water and/or detergent are contained when sprayed from the spray ball 903a. Additionally, a second spray ball 903b may extend into chamber 12. In these embodiments, water and/or detergents may be sprayed onto the underside of the drip tray 32 as well as the walls 14 of the chamber 12. Of course, the interior (e.g. the chamber 12) of the apparatus may be warmed above cryogenic temperatures for cleaning.

Although inlet 35 may be repositioned, inlet 35 may allow the composition to enter the apparatus 10 to be dripped through tray 32. Therefore, cleaning extension 905 may clean composition out of the apparatus 10. For example, routine cleanings and/or cleanings between flavoring changes may be performed.

Figure 10:
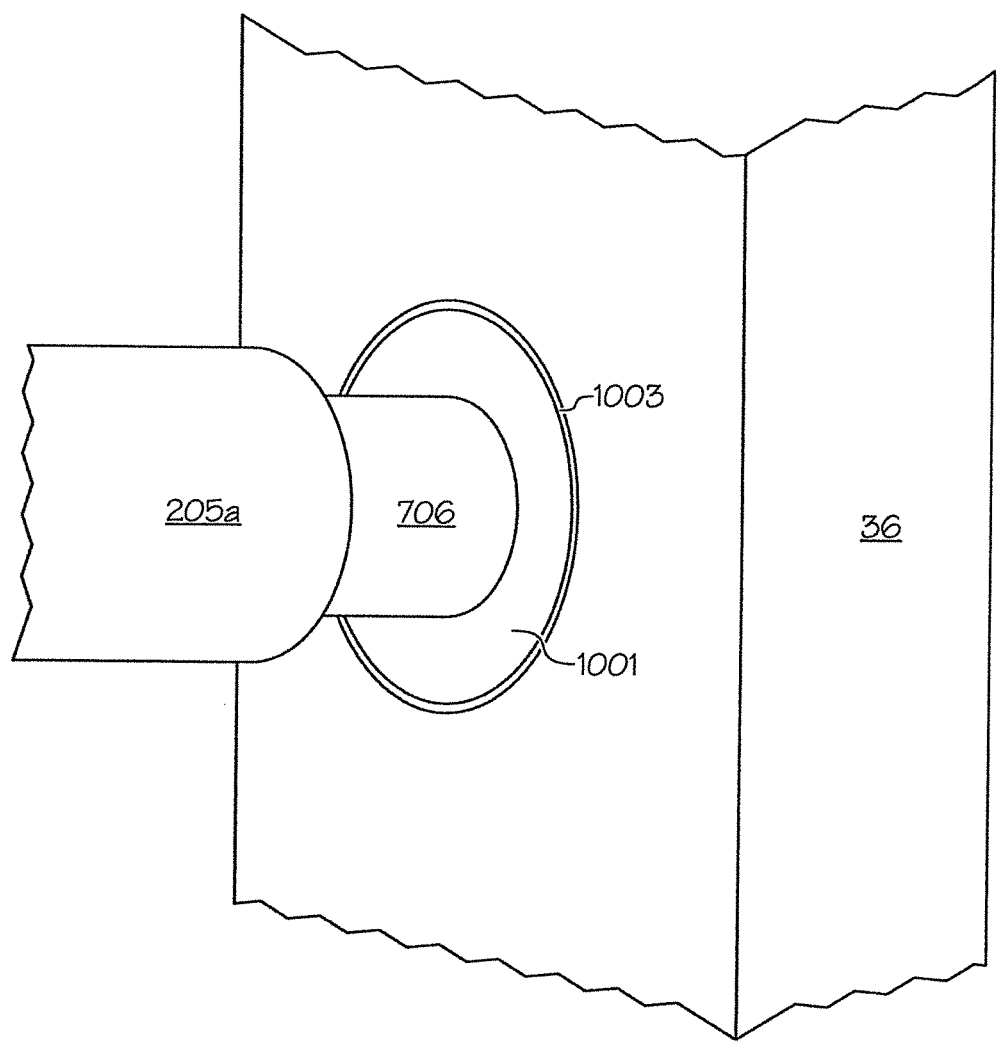
FIG. 10 depicts a diagram of an example interaction of a roller and a housing of the apparatus of FIG. 1 in accordance with the principles of the present invention.

FIG. 10 depicts a diagram of a partially exploded diagram of an example interaction of a roller and a housing of the apparatus of FIG. 1 in accordance with the principles of the present invention. An o-ring recess 1003 may be formed in the interior of the housing 36 such that O-ring 1001 may fit inside. In some embodiments, this fit prevents fluids from entering the o-ring recess and prevents fluid from reaching the axle 706. In some embodiments, the axle 706 may be a smaller diameter than the roller 205a such that the axle 706 fits within o-ring 1001. Thus, a side of roller 205a may be frictionally fit against the o-ring 1001 such that the axle 706 is protected.

The foregoing description has been presented for purposes of illustration and description. It is not intended to be exhaustive or to limit the invention to the precise form disclosed. Obvious modifications or variations are possible in light of the above teachings. The embodiment was chosen and described to provide the best illustration of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally and equitably entitled.

In summary, numerous benefits have been described which result from employing the concepts of the present invention. In particular, a method of the present invention allows the preparation, storing and serving of a unique, free-flowing, frozen supplementary product. Because the product is quick frozen, it can be smoother and creamier and provide a full-bodied flavor. Advantageously, the resulting product may have a certain sophistication that appeals to today's discriminating consumers who want something special.

The previous description is provided to enable any person skilled in the art to practice the various embodiments described herein. Various modifications to these embodiments will be readily apparent to those skilled in the art, and the generic principles defined herein may be applied to other embodiments. Thus, the claims are not intended to be limited to the embodiments shown herein, but are to be accorded the full scope consistent with each claim's language, wherein reference to an element in the singular is not intended to mean "one and only one" unless specifically so stated, but rather "one or more." All structural and functional equivalents to the elements of the various embodiments described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for.

What is claimed is:

1. A method of preparing and storing a free-flowing frozen supplementary product, comprising the steps of:
    preparing a supplementary composition for freezing;
    dripping the supplementary composition into a freezing chamber containing a refrigerant therein;
    freezing the dripped supplementary composition into frozen beads upon contact with the refrigerant, the frozen beads including a plurality of frozen beads of greater than a predetermined size and a plurality of frozen beads of less than the predetermined size;
    draining a product comprising the frozen beads and the refrigerant from the freezing chamber into an intake to an elongated housing, the intake being connected to the freezing chamber, wherein the product exits the freezing chamber and enters the intake prior to entering the elongated housing;
    receiving the product from the intake into an intermediate portion of the elongated housing, the elongated housing having a lower end and an upper end, the upper end being elevated relative to the lower end, wherein the intermediate portion of the elongated housing is between the upper end and the lower end at an intermediate elevation relative to the elevation of the lower end and the elevation of the upper end, the elongated housing further comprising a channel defined within the elongated housing between the lower end and the upper end, wherein the product received from the freezing chamber through the intake contacts a lower portion of a conveyor belt having a mesh surface, the conveyor belt being mounted within the channel adjacent to the intermediate portion for movement between the lower portion and an upper portion within the channel, the upper portion being at a higher elevation than the lower portion, the upper portion being adjacent to the upper end of the elongated housing, wherein a retaining wall defined by the elongated housing from the lower portion to the upper portion is positioned at a straining distance from the mesh surface of the conveyor belt, the straining distance being sized to physically limit movement of the plurality of frozen beads of greater than the predetermined size from the intermediate portion to the lower end of the channel, whereby the plurality of frozen beads of greater than the predetermined size are corralled at the lower portion of the conveyor belt;
    moving the conveyor belt with the product in the elongated housing from the lower portion to the elevated upper portion, wherein the refrigerant in the product in the elongated housing cools the channel within the elongated housing to a temperature below the freezing point of the supplementary composition, whereby the frozen beads in the product in the elongated housing are maintained in frozen form within the channel as the conveyor belt moves from the lower portion to the upper portion;
    sifting the plurality of frozen beads of less than the predetermined size from the frozen beads in the product in the elongated housing and straining the refrigerant from the product in the elongated housing through a plurality of gaps defined in the mesh surface of the conveyor belt as the conveyor belt moves from the lower portion to the upper portion, the mesh surface being sized to enable the plurality of frozen beads of greater than the predetermined size in the product to remain on the mesh surface of the conveyor belt and enable the plurality of frozen beads of less than the predetermined size and the refrigerant in the product to pass through the mesh surface of the conveyor belt as the conveyor belt moves between the lower portion and the upper portion; and
    discharging the plurality of frozen beads of greater than the predetermined size on the conveyor belt at the upper portion by dropping the frozen beads of greater than the predetermined size from the upper portion of the conveyor belt into a chute adjacent to the upper end of the elongated housing.

2. The method of claim 1, wherein the step of sifting the plurality of frozen beads of less than the predetermined size from the frozen beads in the product sifts the frozen beads whereby the plurality of frozen beads of greater than the predetermined size remaining on the conveyor belt are between 2.0 mm and 10.0 mm in diameter.

3. The method of claim 1, wherein the step of sifting the plurality of frozen beads of less than the predetermined size from the frozen beads in the product sifts the frozen beads whereby the plurality of frozen beads of greater than the predetermined size remaining on the conveyor belt are between 2.0 mm and 4.0 mm in diameter.

4. The method of claim 1, further comprising:
    directing the discharged plurality of frozen beads of greater than the predetermined size from the chute into a shaker; and
    selecting one or more frozen beads of the predetermined size from the plurality of frozen beads of greater than the predetermined size by operation of the shaker.

5. The method of claim 1, further comprising:
    storing the discharged plurality of frozen beads of greater than the predetermined size at a temperature at least as low as $-28.9°$ C.

6. The method of claim 5, further comprising:
    bringing the discharged plurality of frozen beads of greater than the predetermined size to a temperature between about $-23.3°$ C. and $-28.9°$ C. prior to serving; and
    serving the discharged plurality of frozen beads of greater than the predetermined size for consumption at a temperature between about $-23.3°$ C. and $-28.9°$ C., whereby the plurality of frozen beads of greater than the predetermined size are free-flowing when served.

7. The method of claim 1, wherein the conveyor belt is positioned from 55 degrees to 60 degrees relative to a horizontal plane.

8. The method of claim 1, wherein the step of sifting the frozen beads of less than the predetermined size from the frozen bead in the product and straining the refrigerant from the product received in the elongated housing through the plurality of gaps defined in the mesh surface of the conveyor belt, further comprises:

sifting the frozen beads of less than the predetermined size against rods of the conveyor belt positioned between rod gaps, the rods and rod gaps being configured to retain the frozen beads of greater than the predetermined size on the conveyor belt as the conveyor belt moves through the channel.

9. The method of claim 8, wherein the predetermined size comprises a diameter of about 2.0 mm to about 10.0 mm.

10. The method of claim 8, wherein the predetermined size comprises a diameter of about 2.0 mm to about 4.0 mm.

11. The method of claim 1, wherein the diameter of the predetermined size is about 2.0 mm to about 10.0 mm.

12. The method of claim 1, wherein the diameter of the predetermined size is about 2.0 mm to about 4.0 mm.

* * * * *